United States Patent
Steinbrenner et al.

(10) Patent No.: US 9,622,470 B2
(45) Date of Patent: Apr. 18, 2017

(54) MICROCAPSULES COMPRISING ANIONIC PESTICIDES

(71) Applicant: BASF SE, Ludwigshafen (DE)

(72) Inventors: Ulrich Steinbrenner, Neustadt (DE); Thorsten Volland, Waldsee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/778,790

(22) PCT Filed: Mar. 26, 2014

(86) PCT No.: PCT/EP2014/056075
§ 371 (c)(1),
(2) Date: Sep. 21, 2015

(87) PCT Pub. No.: WO2014/154757
PCT Pub. Date: Oct. 2, 2014

(65) Prior Publication Data
US 2016/0057995 A1    Mar. 3, 2016

(30) Foreign Application Priority Data
Mar. 26, 2013 (EP) .................... 13161147

(51) Int. Cl.
*A61K 9/16* (2006.01)
*A61K 9/50* (2006.01)
*A01N 25/28* (2006.01)
*A01N 37/40* (2006.01)

(52) U.S. Cl.
CPC ............. *A01N 25/28* (2013.01); *A01N 37/40* (2013.01)

(58) Field of Classification Search
None
See application file for complete search history.

(56) References Cited

U.S. PATENT DOCUMENTS 6,015,571 A    1/2000    Scher et al.

FOREIGN PATENT DOCUMENTS

| EP | 0 517 669 | 12/1992 |
|---|---|---|
| EP | 0 730 406 | 5/1995 |
| WO | WO 91/04661 | 4/1991 |

OTHER PUBLICATIONS

International Search Report dated May 20, 2014, prepared in International Application No. PCT/EP2014/056075.
International Preliminary Report on Patentability dated Jun. 15, 2015, prepared in International Application No. PCT/EP2014/056075.
Odian, G., "*Principles of Polymerization*," 3$^{rd}$ ed., 1991, pp. 132-134.

*Primary Examiner* — Alton Pryor
(74) *Attorney, Agent, or Firm* — Brinks Gilson & Lione

(57) ABSTRACT

Microcapsules comprising a core (a) and a shell (b), wherein the core comprises a salt of an anionic pesticide (a1) and optionally a water immiscible solvent (a2), wherein the cation of the salt of the anionic pesticide is an ammonium, phosphonium or sulfonium cation, wherein the groups on the ammonium, phosphonium or sulfonium cation, taken together contain at least 12 and no more than 50 cation atoms and wherein the ratio of the number of carbon atoms in the group with the largest number of carbon atoms to the average number of carbon atoms of all groups on the N, P or S-atom is less than 3.0.

23 Claims, No Drawings

MICROCAPSULES COMPRISING ANIONIC PESTICIDES

This application is a National Stage application of International Application No. PCT/EP2014/056075 filed Mar. 26, 2014. This application also claims priority under 35 U.S.C. §119 to European Patent Application No. 13161147.7 filed Mar. 26, 2013.

The invention relates to microcapsules comprising an anionic pesticide, a process for preparing such microcapsules, an aqueous composition comprising such microcapsules and a method for controlling pests by applying the composition.

There are various pesticides which have a rather high volatility, such as free acid forms of carboxylic acid containing pesticides like dicamba or 2,4-D. Such volatile pesticides are subject to a higher degree of drift, which could cause damage to sensitive off-target crops (e.g. soybeans) in nearby fields. They are also less effective on target pests, since a large part of the pesticide evaporates. To avoid these problems, low volatile pesticides are desirable. In addition, anionic pesticides more frequently show the problem of leaching, i. e. the undesired penetration of the pesticide into the ground water.

E.g. WO 2012/059 494 and WO 2011/039 172 disclose cationic polyamine salts of anionic pesticides showing a low volatility.

Microcapsules comprising lipophilic pesticides are known, e. g. from WO 2004/017734. Microcapsules comprising different salts of anionic pesticides like dicamba are known from WO 91/04661. The salts are preferably metal salts, and the shell material is a urea-, thiourea- or melamin formaldehyde condensate. EP-A 0 517 669 discloses microcapsules of anionic pesticides made of polyester. The dimethyldodecylamine and dimethylhexadecylamine salts of dicamba are disclosed in this document. EP-A 0 730 406 discloses microcapsules containing pesticides, where the shell material is a polyurea.

Although good results are achieved with such microcapsules, there is still room for improvement in formulation technologies for anionic pesticides.

It has now been found that improved formulations of salts of anionic pesticides as microcapsules can be prepared by specific selection of the cation.

Accordingly, in one aspect of the invention there is provided a microcapsule comprising a core (a) and a shell (b), wherein the core comprises a salt of an anionic pesticide (a1) and optionally a water immiscible solvent (a2), wherein the cation is an ammonium, sulfonium or phosphonium cation, wherein the groups on each N, S or P atom, taken together, contain at least 12 and no more than 50 carbon atoms, and wherein the ratio of the number of carbon atoms in the group with the largest number of carbon atoms on the heteroatom (i. e. N, S or P atom) to the average number of carbon atoms of all groups on the heteroatom is less than 3.0.

A further embodiment of the invention provides a method for preparing the microcapsules of the invention, comprising the steps of mixing an oil phase and a water phase, wherein the oil phase comprises the salt of the anionic pesticide—according to the invention—optionally a solvent, and at least one lipophilic monomer, and the water phase optionally comprises at least one monomer, and polymerizing the monomers at the surface of the oil phase and water phase to form the microcapsules of the invention.

Another embodiment of the invention provides an aqueous composition comprising the microcapsules of the invention.

A further embodiment of the invention provides a method for undesired plant growth and/or controlling phytopathogenic fungi and/or undesired attack by insects or mites and/or for regulating the growth of plants, where the micropasules of the invention or the aqueous composition comprising the microcapsules of the invention is allowed to act on undesired plants and/or on the particular pests, their habitat or the plants to be protected from the particular pest, the soil and/or the useful plants and/or their habitat.

The microcapsules of the invention allow for a low-volatile formulation of anionic pesticides that avoids problems with drift and loss of activity. In addition, the problem of leaching is reduced.

The salt of an anionic pesticide (a1) comprises a the anionic pesticide and—depending on the charge of the anionic pesticide—one or more cations.

The term "anionic pesticide" refers to a pesticide, which is present as an anion. Preferably, anionic pesticide means a pesticide comprising—in the neutral form—a protonizable hydrogen. More preferably, anionic pesticide relates to a pesticide comprising one or more carboxylic, thiocarbonic, sulfonic, sulfinic, thiosulfonic or phosphorous acid groups, especially one or more barboxylic acid groups. The aforementioned groups may be partly present in neutral form including the protonizable hydrogen.

The anionic pesticide comprises at least one anionic group. Preferably, the anionic pesticide comprises one or two anionic groups. In particular the anionic pesticide comprises exactly one anionic group. An example of an anionic group is a carboxylate group ($-C(O)O^-$). Although the anionic pesticide forms a salt in the microcapsules of the invention, the aforementioned anionic groups may be partly present in neutral form in aqueous compositions, in which, e. g. an equilibrium of carboxylate and carboxylic acid may be present. Anionic pesticides are preferred, where at least 50%, preferably at least 70%, more preferred at least 90%, of the anionic pesticide are present in deprotonated form in water at a pH value of 8 at 25° C.

Examples of anionic pesticides which are able to form salts with suitable cations and can be used to prepare the microcapsules of the invention are given in the following. Although the common names used in the following may refer to a neutral form or a salt of the anionic pesticide with a cation not suitable for the invention, the anionic form of the anionic pesticide is meant for the purpose of the invention. For example, the term dicamba refers to the anionic form of dicamba which may be represented by the following formula:

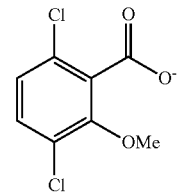 [SMILES: COc1c(Cl)ccc(Cl)c1C(=O)[O-]]

It is known to an expert that the dissociation of the functional groups and thus the location of the anionic charge may depend for example on the pH, when the anionic pesticide is present in dissolved form.

One preferred group of anionic pesticides are herbicides that comprise a carboxylic, thiocarbonic, sulfonic, sulfinic, thiosulfonic or phosphorous acid group, especially a carboxylic acid group. Examples are aromatic acid herbicides, phenoxycarboxylic acid herbicides or organophosphorus herbicides comprising a carboxylic acid group.

Preferred aromatic acid herbicides are benzoic acid herbicides, such as diflufenzopyr, naptalam, chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, clopyralid, picloram; quinolinecarboxylic acid herbicides, such as quinclorac, quinmerac; or other aromatic acid herbicides, such as aminocyclopyrachlor. Preferred are benzoic acid herbicides, especially preferred is dicamba.

Preferred phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxyphenoxypropionic herbicides, such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop. Preferred are phenoxyacetic herbicides, especially MCPA and 2,4-D.

Organophosphorus herbicides comprising a carboxylic acid group include bialafos, glufosinate, glufosinate-P and glyphosate.

Suitable other herbicides comprising a carboxylic acid include pyridine herbicides comprising a carboxylic acid, such as fluroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron; imidazolinone herbicides, such as imazamethabenz, imazamethabenz, imazamox, imazapic, imazapyr, imazaquin and imazethapyr; triazolinone herbicides such as flucarbazone, propoxycarbazone and thiencarbazone; aromatic herbicides such as acifluorfen, bifenox, carfentrazone, flufenpyr, flumiclorac, fluoroglycofen, fluthiacet, lactofen, pyraflufen. Further, chlorflurenol, dalapon, endothal, flamprop, flamprop-M, flupropanate, flurenol, oleic acid, pelargonic acid, TCA may be mentioned as other herbicides comprising a carboxylic acid.

Further suitable anionic pesticides include fungicides that comprise a carboxylic, thiocarbonic, sulfonic, sulfinic, thiosulfonic or phosphorous acid group, especially a carboxylic acid group. Examples are polyoxin fungicides, such as polyoxorim.

Further suitable anionic pesticides include insecticides that comprise a carboxylic, thiocarbonic, sulfonic, sulfinic, thiosulfonic or phosphorous acid group, especially a carboxylic acid group. An example is thuringiensin.

Further suitable anionic pesticides include plant growth regulators that comprise a carboxylic, thiocarbonic, sulfonic, sulfinic, thiosulfonic or phosphorous acid group, especially a carboxylic acid group. Examples are 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, preferably prohexadione and trinexapac.

The skilled worker is familiar with the above referenced pesticides, which are commercial products, and are further described, for example, in The Pesticide Manual, 16th Ed. (2012), The British Crop Protection Council, Alton.

Preferred anionic pesticides are anionic herbicides, more preferred are dicamba, 2,4-D, aminopyralid, aminocyclopyrachlor and MCPA. Especially preferred are dicamba, 2,4-D and MCPA. In one embodiment dicamba is particularly preferred. In another embodiment 2,4-D is particularly preferred. In another embodiment MCPA is particularly preferred.

Suitable cations are hydrophobic enough to make the salt consisting of the anionic pesticide and the cation hardly soluble in water. "Hardly soluble in water" as used herein means a solubility of no more than 30 g/l at 20° C., preferably no more than 10 g/l at 20° C., more preferred no more than 1 g/l at 20° C.

In order to avoid problems in capsule formation—specifically in the case of polyurea capsules—the cation should either contain no reactive group, such as OH, SH, NH, $N^+H_2$ or $N^+H_3$, or such groups should be sterically shielded to prevent them from interfering with the encapsulation agent. One example of such a cation is the di-iso-tridecylammonium cation, which contains a sterically shielded $N^+H_2$ group.

The cation is an ammonium, sulfonium or phosphonium cation comprising in the case of ammonium at least two organic groups in the case of sulfonium three organic groups, and in the case of phosphonium four organic groups. The groups on each N, S or P atom, taken together, contain at least 12, preferably at least 15 carbon atoms. The total number of carbon atoms on each N, S or P atom, taken together, is no more than 50, preferably no more than 30, in particular no more than 24.

A preferred class of cations are secondary, tertiary and quaternary ammonium cations; preferred are tertiary and quaternary ammonium cations.

The organic groups on the ammonium, sulfonium or phosphonium cations as defined herein—are generally linear, branched, cyclic, araliphatic, cycloallyl-alkyl, cycloalkenyl-alkyl moieties which are saturated, unsaturated or aromatic, which comprise—in line with the rules given below—from 1 to 25 carbon atoms, and which further may comprise one or more heteroatoms, preferably selected from O, N and S.

Preferred as organic groups on the cation are linear or branched alkyl groups, preferably with 1 to 22, more preferred 1 to 18 carbon atoms, cycloalkyl groups, preferably with 3 to 8, more preferred 5 or 6 carbon atoms, aromatic groups, preferably with 6 to 12, more preferred 6 carbon atoms, and araliphatic groups, preferably with 7 to 20, more preferred 7 to 15 carbon atoms.

Examples of such groups are methyl, ethyl, n-propyl, i-propyl, n-butyl, s-butyl, t-butyl, n-pentyl, i-pentyl, n-hexyl, n-octyl, n-decyl, n-dodecyl, n-tetradecyl, n-hexadecyl, cyclohexyl, phenyl and benzyl.

Examples of respective ammonium cations are tri-n-butylammonium, tri-n-pentylammonium, tri-i-pentylammonium, tri-n-hexylammonium, tri-n-octylammonium, methyl-di-n-octylammonium, methyl-di-n-decylammonium, tri-benzylammonium and tri-2-ethylhexylammonium.

Organic groups containing one or more heteroatoms are preferably oligo- or polyalkylene oxides, preferably oligoor polypropylene oxides, or polybutylene oxides, or mixed oligo- or polypropylene-butylene oxides.

Further, the cation is an ammonium, sulfonium or phosphonium, preferably ammonium cation, where the ratio of the number of carbon atoms of the group with the largest number of carbon atoms on the heteroatom (i. e. N, S or P atom) to the average number of carbon atoms of all groups on the heteroatom (i.e. organic groups and other groups like H) is less than 3.0, preferably less than 2.5, more preferred less than 2.0. It is also preferred that the ratio is at least 1.4.

By way of example, in the methyl-di-n-octylammonium cation the group with the largest number of carbon atoms has 8 carbon atoms, the average number of carbon atoms for the four groups is (1+8+8+0)/4=4.25. The ratio is 8/4.25=1.88. Accordingly, methyl-di-n-octylammonium is a more preferred cation. Likewise, for tri-benzylammonium, the group with the largest number of carbon atoms has 7 carbon atoms, the average number of carbon atoms for the four groups is (7+7+7+0)/4=5.25. The ratio is 7/5.25=1.33. Accordingly, tri-benzylammonium is a more preferred cation. For di-iso-tridecylammonium the group with the largest number of carbon atoms has 13 carbon atoms, the average number of carbon atoms for the four groups is (13+13+0+0)/4=6.5. The ratio is 13/6.5=2. Accordingly, di-iso-tridecylammonium is a preferred cation.

The salt of the anionic pesticide has preferably a solubility in water of less than 30 g/l at 20° C. More preferably, it has solubility of less than 10 g/l, in particular of less than 1 g/l.

The salt of the anionic pesticide has usually a solubility in a mixture of aromatic hydrocarbons with a distillation range of 235-290° C. (e.g. Solvesso® 200 ND) of at least 20 wt %, preferably at least 30 wt %, and in particular at least 50 wt %, at 20° C.

The core of the microcapsules optionally comprises a water-immiscible solvent (a2). Preferably, solvent (a2) has a solubility in water of up to 20 g/l at 20° C., more preferably of up to 5 g/l and in particular of up to 0.5 g/l. Usually, solvent (a2) has a boiling point above 100° C., preferably above 150° C., and in particular above 180° C. (at 1 bar).

"Solvent" in this case means that the solvent (a2) is able to form a homogeneous mixture with the salt (a1) of the anionic pesticide or dissolve it.

Preferred as solvent are:
- an aromatic hydrocarbon solvent such as toluene, xylene, tetrahydronaphthalene, or an alkylated naphthalene or derivative thereof;—
- a fatty acid ester, such as $C_1$-$C_{10}$-alkylester of a $C_{10}$-$C_{22}$-fatty acid or methyl- or ethyl esters of vegetable oils such as rapeseed oil methyl ester or corn oil methyl ester, or glycerides like vegetable oils such as corn oil or rapeseed oil,
- a fatty acid dialkyl amide, such as a $C_1$-$C_{10}$-dialkyl amide of a $C_{10}$-$C_{22}$-fatty acid.

Paraffines are not used as solvents of the invention.

Mixtures of the aforementioned solvents are also possible. The water-immiscible solvent (a2) is usually commercially available, such as aromatic hydrocarbons under the tradenames Solvesso® 200, Aromatic® 200, or Caromax® 28. The aromatic hydrocarbons may be used as naphthalene depleted qualities.

An example of commercially available fatty acid esters is methyl oleate (e.g. Synative® ES METI 05, Cognis, Germany).

Examples of commercially available fatty acid dialkyl amides are octanoic acid, decanoic acid dimethylamide (e.g. Genagen® 4296, Clariant, Germany) and dodecanoic acid.

Preferred solvents (a2) are aromatic hydrocarbons, fatty acid esters and fatty acid amides, as described above.

Apart from the salt of the anionic pesticide (a1) and the optional solvent (a2), the core may comprise further solvents, not included in the list of solvents (a2), however, this is not preferred.

In one embodiment of the invention the core does not comprise a water immiscible solvent (a2), i.e., apart from auxiliaries the core consists of one or more, preferably one, salt of an anionic pesticide.

In a further preferred embodiment the core comprises a water immiscible solvent (a2).

In this embodiment the salt of the anionic pesticide may be present in the core in dissolved form, as suspension, emulsion or suspoemulsion. Preferably, the salt of the anionic pesticide is present in dissolved form. Further, in this embodiment the weight ratio of the salt of the anionic pesticide in the core (or of the sum of all salts in case more than one is present in the core) to the sum of all solvents (e.g. solvent (a2) and any cosolvent) in the core is typically from 5:1 to 1:10, preferably from 3:1 to 1:2, more preferably from 2:1 to 1:1.

The core contains at least 10 wt %, preferably at least 30 wt % and in particular at least 50 wt % of the salt of the anionic pesticide, based on the total amount of the core materials. The core may contain up to 100 wt %, preferably up to 70 wt % of the salt of the anionic pesticide. The amount of core materials is typically summed up from the amounts of all salts of anionic pesticides and any solvents in the core.

Suitable shell materials are well known to someone skilled in the art and include, inter alia, polyacrylates (S1), polystyrenes (S2), melamin formaldehyde condensates (S3) and polyaddition products of isocyanates, in particular polyureas (S4). Preferred are polyaddition products of polyacrylates (S1), polystyrenes (S2) and polyaddition products of isocyanates. More preferred are polyaddition products of isocyanates (S4) with polyureas being particularly preferred.

Preferred polyacrylates (S1) are obtainable by polymerization of

M1.1) 30 to 100% by weight, based on S1, of at least one monomer (M I) selected from the group of the $C_1$-$C_{24}$-alkyl esters of acrylic acid, $C_1$-$C_{24}$-alkyl esters of methacrylic acid and methacrylonitrile, M1.2) 0 to 70% by weight, based on S1, of at least one monomer (M II), selected from the group of polyfunctional monomers, and M1.3) 0 to 40% by weight, based on S1, of at least one further monomer (M III) which is structurally different from monomers (M I) and (M II).

Preferred as monomers (M I) are $C_1$-$C_{24}$-alkyl esters of acrylic and methacrylic acid, and also methacrylonitrile. Preferred monomers (M I) are methyl acrylate, ethyl acrylate, n-propyl acrylate, isopropyl acrylate, n-butyl acrylate, isobutyl acrylate, sec-butyl acrylate and tert-butyl acrylate and stearyl acrylate, and also methyl methacrylate, ethyl methacrylate, n-propyl methacrylate, isopropyl methacrylate, n-butyl methacrylate, isobutyl methacrylate, sec-butyl methacrylate, tert-butyl methacrylate and methacrylonitrile and mixtures of the monomers mentioned above. From among the monomers mentioned above, preference is given to the methacrylates. Particular preference is given to methyl acrylate, ethyl acrylate, isopropyl acrylate, n-butyl acrylate and tert-butyl acrylate and methyl methacrylate, ethyl methacrylate, isopropyl methacrylate, n-butyl methacrylate, tert-butyl methacrylate and stearyl acrylate. Methyl methacrylate, n-butyl acrylate and stearyl acrylate are especially preferred.

Suitable monomers (M II) are polyfunctional monomers which are sparingly soluble, if at all, in water but have good to limited solubility in lipophilc substances. The sparing solubility of the monomers (M II) is to be understood as meaning a solubility of <60 g/l at 20° C. and 1013 mbar in water.

In the context of the invention, polyfunctional monomers are understood as meaning monomers having at least two non-conjugated double bonds. Preferred polyfunctional monomers are divinyl or polyvinyl monomers; esters of diols or polyols with acrylic acid; esters of diols or polyols with methacrylic acid; ethers of diols or polyols and allyl alcohol and ethers of diols or polyols and vinyl alcohol.

Particularly preferred monomers (M II) having two non-conjugated double bonds are 1,2-ethanediol diacrylate, 1,3-propanediol diacrylate, 1,4-butanediol diacrylate, 1,5-pentanediol diacrylate and 1,6-hexanediol diacrylate, 1,2-ethanediol dimethacrylate, 1,3-propanediol dimethacrylate, 1,4-butanediol dimethacrylate, 1,5-pentanediol dimethacrylate and 1,6-hexanediol dimethacrylate, divinylbenzene, ethylene glycol dimethacrylate, 1,3-butylene glycol dimethacrylate, methallylmethacrylamid and allyl methacrylate. Very particular preference is given to 1,3-propanediol diacrylate, 1,4-butanediol diacrylate, 1,5-pentanediol diacrylate and 1,6-hexanediol diacrylate, 1,3-propanediol dimethacrylate, 1,4-butanediol dimethacrylate, 1,5-pentanediol dimethacrylate and 1,6-hexanediol dimethacrylate.

Preferred monomers (M II) having more than two non-conjugated double bonds are trimethylolpropane triacrylate, trimethylolpropane trimethacrylate, pentaerythritol triallyl ether, pentaerythritol triacrylate and pentaerythritol tetraacrylate and mixtures thereof.

Suitable monomers (M III) are monomers IIIa) such as butanediene, isoprene, vinyl acetate, vinyl propionate and vinylpyrridine and IIIb) water-soluble monomers such as acrylonitrile, methacrylamide, acrylic acid, methacrylic acid, itaconic acid, maleinic acid, maleic anhydride, N-vinylpyrrolidone, 2-hydroxyethyl acrylate, 2-hydroxyethyl methacrylate and acrylamido-2-methylpropanesulfonic acid, N-methylolacrylamide, N-methylolmethacrylamide, dimethylaminoethyl methacrylate and diethylaminoethyl methacrylate. Especially suitable are N-methylolacrylamide, N-methylolmethacrylamide, dimethylaminoethyl methacrylate and diethylaminoethyl methacrylate. Particular preference is given to the free acids, i.e. acrylic acid and in particular methacrylic acid, of the acrylates mentioned under M I.

More preferred polyacrylates S1 can be obtained by polymerization of

M1.1) 30 to 100% by weight based on S1, of at least one monomer (M I) selected from the group consisting of methyl acrylate, ethyl acrylate, isopropyl acrylate, n-butyl acrylate and tert-butyl acrylate and methyl methacrylate, ethyl methacrylate, isopropyl methacrylate, n-butyl methacrylate, tert-butyl methacrylate and stearyl acrylate;

M1.2) 0 to 70% by weight, based on S1, of at least one monomer (M II) selected from the group consisting of butanediol diacrylate, trimethylolpropane triacrylate, trimethylolpropane trimethacrylate, pentaerythritol triallyl ether, pentaerythritol triacrylate and pentaerythritol tetraacrylate and also M1.3.) 0 to 40% by weight, based on S1, of acrylic acid and/or methacrylic acid.

Particularly preferred polyacrylates S1 can be obtained by polymerization of

M1.1) 30-100% by weight based on S1, of at least one monomer (M I) selected from the group consisting of methyl methacrylate, stearyl acrylate and n-butyl acrylate;

M1.2) 0 to 70% by weight, based on S1, of at least one monomer (M II) selected from the group consisting of butanediol diacrylate, trimethylolpropane triacrylate, trimethylolpropane trimethacrylate, pentaerythritol triallyl ether, pentaerythritol triacrylate and pentaerythritol tetraacrylate and also M1.3) 0 to 40% by weight, based on S1, acrylic acid or methacrylic acid.

Polyacrylates S1 can be obtained by processes known to the person skilled in the art, for example by free-radical, anionic or cationic polymerization in the absence of a solvent, in a solution, in a dispersion or in an emulsion. Preference is given to free-radical polymerization. Particular preference is given to aqueous free-radical emulsion polymerization, suspension polymerization and aqueous free-radical mini-emulsion polymerization. In a particularly preferred embodiment, the polymer particle comprises, as component M1.3 (M III), methacrylic acid in amounts of 1-50% by weight, preferably 1-20% by weight, in each case based on S1.

Suitable polystyrenes S2 can be obtained by polymerization of

M2.1) 30 to 100% by weight, based on S2, of at least one styrene derivative (M IV), M2.2) 0-70% by weight, based on S2, of at least one vinyl monomer (M V) which is different from monomer (M IV), and M2.3) 0-40% by weight, based on S2, of at least one monomer (M VI) which is different from monomers (M IV) and (M V).

Suitable monomers (M IV) are, for example, styrene, alpha-methylstyrene, beta-methylstyrene and ring-substituted alkylstyrenes. Preferred monomers (M IV) are styrene, alpha-methylstyrene and beta-methylstyrene. Styrene is especially preferred.

Suitable monomers (M V) are, preferably, compounds having two or more non-conjugated double bonds, such as butanediol vinyl ether, diethylene glycol divinyl ether, triethylene glycol divinyl ether, cyclohexanedimethanol divinyl ether and allyl methacrylate.

Suitable monomers (M VI) are, preferably, methyl vinyl ether, ethyl vinyl ether, n-butyl vinyl ether, isobutyl vinyl ether and tert-butyl vinyl ether, and also vinyl acetate.

Polymer S2 can likewise be obtained by the methods described for S1, which are known to the person skilled in the art.

Preferred melamin formaldehyde condensates S3 are obtainable by polycondensation M3.1) melamine formaldehyde prepolymers (M VII) and/or M3.2) alkyl ethers of melamine formaldehyde prepolymers (M VIII).

Polymers S3 can be obtained by known polycondensation reactions which are familiar to the person skilled in the art. The preparation of melamine formaldehyde resins and capsules is described, for example, in EP 0 974 394, U.S. Pat. No. 4,172,119, EP-A 0 026 914 and EP-A 0 218 887.

Preferred polyaddition products of isocyanates S4 can be obtained by polyaddition of M4.1) 30-100% by weight, based on S4, of at least one isocyanate derivative (M XIII), M4.2) 0-70% by weight, based on S4, of at least one amino compound (M XIV), and/or M4.3) 0-70% by weight, based on S4, of at least one alcohol (M XV).

Suitable isocyanate derivatives (M XIII) are all isocyanates having two or more isocyanate groups. Preferred are isocyanates listed below for polyurea shells materials.

Suitable amino compounds (M XIV) are guanidine and its salts, di- and polyamines and aminoalcohols. Preference is given to diethylenetriamine, N,N'-bis-(3-aminopropyl)ethylenediamine, hexamethylenediamine (HMDA) and ethylenediamine (EDA).

Suitable alcohols (M XV) are all di- and polyalcohols. Suitable are furthermore ethoxylated and propoxylated di- and polyalcohols. In case the amount of M4.1 is 100% by weight, the reaction partner is water.

Polyaddition processes and the associated monomers (M XII-MXV) are described, for example, in U.S. Pat. No. 4,021,595, EP 0 392 876 and EP 0 535 384.

Particularly preferred are capsules with encapsulation material comprising polyurea, which are well known and can be prepared by analogy to prior art. They are preferably prepared by an interfacial polymerization process of a suitable polymer wall forming material, such as a polyisocyanate and a polyamine. Interfacial polymerization is usually performed in an aqueous oil-inwater emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained. Suitable methods for interfacial polymerization processes for preparing microcapsules containing pesticide compounds have been disclosed in prior art.

In general, polyurea is formed by reacting a polyisocyanate having at least two isocyanate groups with a polyamine having at least two primary amino groups to form a polyurea wall material. In a further embodiment, the polyurea may be formed by contacting polyisocyanate with water. Preferably, the polyurea shell contains a polyisocyanate and a polyamine in polycondensed form. Suitable polyisocyanates are known, e.g. from US 2010/0248963 A1, paragraphs [0135] to [0158], to which full reference is made. Suitable polyamines are known, e.g. from US 2010/0248963 A1, paragraphs [0159] to [0169], to which full reference is made.

Polyisocyanates may be used individually or as mixtures of two or more polyisocyanates. Suitable polyisocyanates are for example aliphatic isocyanates or aromatic isocyanates. These isocyanates may be present as monomeric or oligomeric isocyanates. The NCO content may be determined according to ASTM D 5155-96 A.

Examples of suitable aliphatic diisocyanates include tetramethylene diisocyanate, pentamethylene diisocyanate and hexamethylene diisocyanate as well as cycloaliphatic isocycantates such as isophoronediisocyanate, 1,4-bisisocyanatocyclohexane and bis-(4-isocyanatocyclohexyl)methane.

Suitable aromatic isocyanates include toluene diisocyanates (TDI: a mixture of the 2,4- and 2,6-isomers), diphenylmethene-4,4'-diisocyanate (MDI), polymethylene polyphenyl isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4''-triphenylmethane triisocyanate. Also suitable are higher oligomers of the aforementioned diisocyanates such as the isocyanurates and biurethes of the aforementioned diisocyanates and mixtures thereof with the aforementioned diisocyanates.

In another preferred embodiment, the polyisocyanate is an oligomeric isocyanate, preferably an aromatic, oligomeric isocyanate. Such oligomeric isocyanates may comprise above mentioned aliphatic diisocyanates and/or aromatic isocyanates in oligomerized form. The oligomeric isocyanates have an average functionality in the range of 2.0 to 4.0, preferably 2.1 to 3.2, an more preferably 2.3 to 3.0. Typically, these oligomeric isocyanates have a viscosity (determined according to DIN 53018) in the range from 20 to 1000 mPas, more preferably from 80 to 500 mPas and especially from 150 to 320 mPas. Such oligomeric isocyanates are commercially available, for example from BASF SE under the tradenames Lupranat® M10, Lupranat® M20, Lupranat® M50, Lupranat® M70, Lupranat® M200, Lupranat® MM103 or from Bayer AG as Basonat® A270.

Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol and mixtures thereof with the aforementioned diisocyanates. In this way, several molecules of diisocyanate are linked through urethane groups to the polyhydric alcohol to form high molecular weight polyisocyanates. A particularly suitable product of this kind, DESMODUR® L (Bayer Corp., Pittsburgh), can be prepared by reacting three moles of toluene diisocyanate with one mole of 2-ethylglycerol (1,1-bismethylolpropane). Further suitable products are obtained by addi-tion of hexamethylene diisocyanate or isophorone diisocyanate with ethylene glycol or glycerol.

Preferred polyisocyanates are isophorone diisocyanate, diphenylmethane-4,4'-diisocyanate, toluene diisocyanates, and oligomeric isocyanates, whereas oligomeric isocyanates are in particular preferred.

Suitable polyamines within the scope of this invention will be understood as meaning in general those compounds that contain two and more amino groups in the molecule, which amino groups may be linked to aliphatic or aromatic moieties.

Examples of suitable aliphatic polyamines are α,ω-diamines of the formula $H_2N-(CH_2)_n-NH_2$, wherein n is an integer from 2 to 6. Exemplary of such diamines are ethylenediamine, propylene-1,3-diamine, tetramethylenediamine, pentamethylenediamine and hexame-thylenediamine. A preferred diamine is hexamethylenediamine. Further suitable aliphatic polyamines are polyethylenimines of the formula $H_2N-(CH_2-CH_2-NH)_n-H$, wherein n is an integer from 2 to 20, preferably 3 to 5. Representative examples of such polyethylenimines are diethylenetriamine, triethylenetetramine, tetraethylenepentamine and pentaethylenehexamine. Further suitable aliphatic polyamines are dioxaalkane-α,ω-diamines, such as 4,9-dioxadodecane-1,12-diamine of the formula $H_2N-(CH_2)_3O-(CH_2)_4O-(CH_2)_3-NH_2$.

Examples of suitable aromatic polyamines are 1,3-phenylenediamine, 2,4- and 2,6-toluenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone. Those polyamines which are insoluble or insufficiently soluble in water may be used as their hydrochloride salts.

Polyamines, such as those mentioned above may be used individually or as mixtures of two or more polyamines. Preferred polyamine is a polyethylenimine, such as tetraethylenepentamine.

The relative amounts of each complementary wall-forming component will vary with their equivalent weights. In general, approximately stoichiometric amounts are preferred, while an excess of one component may also be employed, especially an excess of polyisocyanate. The total amount of wall-forming components approximately corresponds to the total amount of polymeric wall-forming materials.

The average particle size of the capsules (z-average by means of light scattering; preferably a $D_{4,3}$ average) is 0.5 to 50 µm, preferably 0.5 to 20 µm, more preferably 1 to 10 µm, and especially 1 to 8 µm.

The invention further relates to a method for preparing the microcapsules of the invention, comprising the steps of
a) mixing a salt of an anionic pesticide or its precursors, i. e. anionic pesticide and an amine, sulfide or phosphane, optionally a water immiscible solvent, water and encapsulating agents,
b) adding a non-ionic or cationic surfactant as emulsifier,
c) emulsifying the mixture, and
d) optionally adding further encapsulation agents and polymerizing the encapsulation agents to form the microcapsules.

Surfactants which are suitable as emulsifiers are nonionic and cationic surfactants. Nonionic surfactants are preferred.

Suitable nonionic surfactants are alkoxylates, N-alkylated fatty acid amides, amine oxides, esters or sugar-based surfactants. Examples of alkoxylates are compounds such as alcohols, alkylphenols, amines (e.g. tallow amine), amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of suitable cationic surfactants are quaternary surfactants, for example quaternary ammonium compounds with one or two hydrophobic groups, or salts of long-chain primary amines. Particularly preferred are non-ionic surfactants where the hydrophobic part consists of alkyl, aralkyl, propylene oxide or butylene oxide, while the hydrophilic part consists of ethylene oxide or ethylene oxide/propylene oxide units.

The invention further provides an aqueous composition comprising the microcapsules according to the invention. In one embodiment this composition comprises a non-encapsulated pesticide. This non-encapsulated pesticide may be present in dissolved form, or as a suspension, emulsion or suspoemulsion. Preferably, it is different to the pesticide in the core.

The aqueous composition contains usually from 5 to 80 wt % of the microcapsules, preferably from 10 to 60 wt %. The aqueous composition contains usually at least 2 wt % encapsulated pesticide, preferably at least 5 wt % and in particular at least 8 wt %. Typically, the composition comprises from 0.5 to 25 wt %, preferably from 1.0 to 20 wt % and in particular from 2.0 to 15 wt % surface-active substances. Preferred surface-active substances are those listed above. Specific examples are Atlas® G 5000, Tween® 20, Soprophor® S 25, Soprophor® BSU, Pluronic® PE 6400, Pluronic® PE 6800, Pluronic® PE 10500, Luviskol® VA 64, Luvitek® K30, Lutensol® TO 10, Lutensol® ON 70, Emulsogen® 35010.

The aqueous compositions according to the invention may also comprise auxiliaries which are customary in agrochemical formulations. The auxiliaries used depend on the particular application form and active substance, respectively. Examples for suitable auxiliaries are dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable surface-active substances (adjuvants, wetters, stickers, dispersants or emulsifiers) are preferably the ones listed above.

Examples for thickeners (i. e. compounds that impart a modified flowability to compositions, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidons, polyvinylacetates, polyvinyl alcohols and cellulose ethers (Tylose®, Shin-Etsu, Japan).

The invention further relates to a method for controlling undesired plant growth and/or phytopathogenic fungi and/or undesired attack by arthropods or helminthes and/or for regulating the growth of plants, where the microcapsules or the aqueous composition according to the invention is allowed to act on the soil and/or on undesired plants, the particular pests, their habitat or the plants to be protected from the particular pest, and/or the useful plants and/or their habitat.

The arthropods or helminths are preferably selected from harmful insects, arachnids and nematodes, more preferably from harmful insects, acarids and nematodes, and even more preferably from harmful insects, mites and nematodes, wherein harmful insects are most preferred.

Various cultivated plants can be protected or treated, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g.

conifers; and on the plant propagation material, such as seeds, and the crop material of these plants.

Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material.

The microcapsules or the aqueous composition can be used as such or in the form of their agrochemical formulations, e. g. in the form of directly sprayable solutions, suspensions, dispersions, emulsions, oil dispersions, by means of spraying, atomizing, dusting, spreading, brushing, immersing or pouring. The application forms depend entirely on the intended purposes; it is intended to ensure in each case the finest possible distribution of the anionic pesticides. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of anionic pesticide(s) ("active substance") applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e. g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the aqueous compositions, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®.

The invention has various advantages: The invention increases the stability of the formulation within broad range of temperatures; it improves compatibility with other pesticides; it reduces the wind drift; the encapsulated active ingredients are effectively protected from UV-light; the capsules may be loaded with both oil and water soluble active ingredients and adjuvants; the capsules have a increased rainfastness; there is a reduced toxicological effect for the worker and users; the formulation is very stable against UV-light or sunlight; the capsules have a high physical stability; the formulation has a excellent biodelivery; the formulation has a very low toxicology (e.g. no ey irritation); the formulation has a low contact angle of the sprayed drops on leaves; the formulation has a high spreading on leaves.

The examples below give further illustration of the invention, which is not, however, restricted to these examples.

EXAMPLES

Starting Materials

Dicamba (acid)
Tri-2-ethyl-hexyl amine (TEHA)
Lupranat® M20S: MDI based polyisocyanate: solvent free polyisocyanate based on 4,4'-diphenylmethane diisocyanate (MDI) with an average functionality of 2,7, NCO content 32 g/100 g.
Solvesso® 200ND: aromatic hydrocarbon solvent, distillation range 235-295° C., freezing point −10 to −20° C., naphthalene content below 1 wt %.
Atlas G 5000 nonionic polyalkylene glycol ether (block copolymer), Croda International, UK (emulsifier)
Rhodopol® G xanthan gum (thickener) Rhodia, France
Acticide® MBS, Thor GmbH, Germany (biocide)

Example 1

Preparation of Capsules (wt.-% refer to the total of the listed ingredients)
Oil Phase:

| | |
|---|---|
| 9.30 wt.-% | dicamba (acid) |
| 15.70 wt.-% | tri-2-ethylhexyl amine |
| 25 wt.-% | Solvesso ® 200 ND |
| 1.0 wt.-% | Lupranat ® M20S |

Aqueous Phase:

| | |
|---|---|
| 0.87 wt.-% | hexamethylenediamine |
| 50 wt.-% | water |
| 2.00 wt.-% | Atlas ® G 5000 |

Auxiliaries

| | |
|---|---|
| 0.01 wt.-% | Acticide ® MBS |
| 0.02 wt.-% | Rhodopol ® G |

The oil phase was added to the aqueous phase and dispersed with a dissolver stirrer at 6000 rpm. The emulsion was heated for 1.5 h at 40° C. The auxiliaries were added. After cooling to room temperature a suspension of capsules was obtained. The average particle size D[90] was 2.6 µm.

The invention claimed is:
1. Microcapsules comprising a core (a) and a shell (b), wherein the core comprises a salt of an anionic pesticide (a1) in dissolved form and a water immiscible solvent (a2) having a solubility in water of up to 20 g/l at 20° C., wherein the cation of the salt of the anionic pesticide is an ammonium, phosphonium or sulfonium cation, wherein the groups on the ammonium, phosphonium or sulfonium cation, taken together contain at least 12 and no more than 50 carbon atoms and wherein the ratio of the number of carbon atoms in the group with the largest number of carbon atoms to the average number of carbon atoms of all groups on the N, P or S-atom is less than 3.0, wherein the shell (b) is a polyurea shell.

2. The microcapsules according to claim 1, wherein the anionic pesticide is a herbicide.

3. The microcapsules according to claim 2, wherein the anionic herbicide is a benzoic acid herbicide or a phenoxycarboxylic acid herbicide.

4. The microcapsules according to claim 3, wherein the anionic herbicide is selected from dicamba, MCPA and 2,4-D.

5. The microcapsules according to claim 4, wherein the anionic herbicide is dicamba.

6. The microcapsules according to claim 1, wherein the groups on the ammonium, phosphonium or sulfonium cation, taken together contain at least 15 carbon atoms.

7. The microcapsules according to claim 1, wherein the groups on the ammonium, phosphonium or sulfonium cation, taken together contain no more than 30 carbon atoms.

8. The microcapsules according to claim 1, wherein the ratio of the number of carbon atoms in the group with the largest number of carbon atoms to the average number of carbon atoms of all groups on the N, P or S-atom is less than 2.5.

9. The microcapsules according to claim 1, wherein the ratio of the number of carbon atoms in the group with the largest number of carbon atoms to the average number of carbon atoms of all groups on the N, P or S-atom is at least 1.4.

10. The microcapsules according to claim 1, wherein the cation of the salt of the anionic pesticide is an ammonium cation.

11. The microcapsules according to claim 1, wherein the additional solvent (a2) is selected from aromatic hydrocarbon solvents, $C_1$-$C_{10}$-alkylesters of $C_{10}$-$C_{22}$-fatty acids and $C_1$-$C_{10}$-dialkyl amides of $C_{10}$-$C_{22}$-fatty acids.

12. A method for preparing microcapsules according to claim 1 comprising the steps of mixing an oil phase and a water phase, wherein the oil phase comprises the salt of the anionic pesticide, the anionic pesticide and an amine, sulphide or phosphane, the solvent, and at least one lipophilic monomer, and the water phase optionally comprises at least one monomer, and polymerizing the monomers at the surface of the oil phase and water phase to form the microcapsules.

13. An aqueous composition comprising the microcapsules as defined in claim 1.

14. A method for controlling undesired plant growth and/or phytopathogenic fungi and/or undesired attack by arthropods and/or helminths and/or for regulating the growth of plants, where the microcapsules as defined in claim 1 is applied to soil and/or on the undesired plants, the fungi, arthropods and/or helminths, their habitat or the plants and/or useful plants, their habitat.

15. The method according to claim 14, wherein the anionic pesticide is a herbicide.

16. The method according to claim 15, wherein the anionic herbicide is a benzoic acid herbicide or a phenoxycarboxylic acid herbicide.

17. The method according to claim 16, wherein the anionic herbicide is selected from dicamba, MCPA and 2,4-D.

18. The method according to claim 17, wherein the anionic herbicide is dicamba.

19. The method according to claim 14, wherein the groups on the ammonium, phosphonium or sulfonium cation, taken together contain at least 15 carbon atoms.

20. The method according to claim 14, wherein the groups on the ammonium, phosphonium or sulfonium cation, taken together contain no more than 30 carbon atoms.

21. The method according to claim 14, wherein the ratio of the number of carbon atoms in the group with the largest number of carbon atoms to the average number of carbon atoms of all groups on the N, P or S-atom is less than 2.5.

22. The method according to claim 14, wherein the ratio of the number of carbon atoms in the group with the largest number of carbon atoms to the average number of carbon atoms of all groups on the N, P or S-atom is at least 14.

23. A method for controlling undesired plant growth and/or phytopathogenic fungi and/or undesired attack by arthropods and/or helminths and/or for regulating the growth of plants, wherein the aqueous composition as defined in claim 13 is applied to soil and/or on undesired plants, the fungi, arthropods and/or helminths, their habitat or the plants and/or useful plants, their habitat.

* * * * *